(12) United States Patent
Lin

(10) Patent No.: US 6,340,766 B1
(45) Date of Patent: Jan. 22, 2002

(54) SUBSTITUTED NAPTHOPYRANS

(75) Inventor: Jibin Lin, Fremont, CA (US)

(73) Assignee: Transition Optical, Inc., Pinellas Park, FL (US)

( * ) Notice: Subject to any disclaimer, the term of this patent is extended or adjusted under 35 U.S.C. 154(b) by 0 days.

(21) Appl. No.: 09/738,175

(22) Filed: Dec. 15, 2000

Related U.S. Application Data

(60) Provisional application No. 60/175,640, filed on Jan. 12, 2000.

(51) Int. Cl.[7] .................. C07D 311/92; G02B 5/23; C08K 5/15; G02C 7/10; G02F 1/03
(52) U.S. Cl. .................. 549/389; 252/586; 524/110; 351/163; 359/241; 428/500
(58) Field of Search .................. 549/389; 252/586; 524/110; 351/163; 359/241; 428/500

(56) References Cited

U.S. PATENT DOCUMENTS

| | | | |
|---|---|---|---|
| 3,567,605 A | 3/1971 | Becker | 204/158 |
| 3,627,690 A | 12/1971 | Casella et al. | 252/300 |
| 4,286,957 A | 9/1981 | Le Naour-Sene | 8/471 |
| 4,880,667 A | 11/1989 | Welch | 427/160 |
| 5,066,818 A | 11/1991 | Gemert et al. | 549/389 |
| 5,185,390 A | 2/1993 | Fischer et al. | 524/43 |
| 5,274,132 A | 12/1993 | VanGemert | 549/389 |
| 5,391,327 A | 2/1995 | Ligas et al. | 252/586 |
| 5,458,814 A | 10/1995 | Kumar et al. | 252/586 |
| 5,573,712 A | 11/1996 | Kumar et al. | 252/586 |
| 5,645,767 A | 7/1997 | Van Gemert | 252/586 |
| 5,650,098 A | 7/1997 | Kumar et al. | 252/586 |
| 5,656,206 A | 8/1997 | Knowles et al. | 252/586 |
| 5,658,500 A | 8/1997 | Kumar et al. | 252/586 |
| 5,753,146 A | 5/1998 | Van Germet et al. | 252/586 |
| 5,770,115 A | 6/1998 | Misura | 252/586 |
| 5,789,015 A | 8/1998 | Gupta et al. | 427/162 |
| 5,936,016 A | 8/1999 | Lareginie et al. | 524/94 |
| 5,975,696 A | 11/1999 | Kohan | 351/177 |
| 6,096,246 A * | 8/2000 | Chan et al. | 252/586 |
| 6,106,744 A | 8/2000 | Van Germet et al. | 252/586 |
| 6,113,814 A * | 9/2000 | Gemert et al. | 252/586 |
| 6,153,126 A | 11/2000 | Kumar | 252/586 |
| 6,197,225 B1 * | 3/2001 | Tanizawa et al. | 252/586 |
| 6,211,374 B1 * | 4/2001 | Ippoliti | 546/153 |
| 6,281,366 B1 * | 8/2001 | Frigoli et al. | 549/59 |
| 6,294,112 B1 * | 9/2001 | Clarke et al. | 252/586 |

FOREIGN PATENT DOCUMENTS

| | | |
|---|---|---|
| WO | WO 98/04937 | 2/1998 |

OTHER PUBLICATIONS

*Freidel–Crafts and Related Reactions*, George Olah, Interscience Publishers, 1964, vol. 3, Chapter XXXI (Aromatic Ketone Synthesis).

"Regioselective Friedel–Crafts Acylation of 1,2,3,4–Tetrahydroquinline and Related Nitrogen Heterocycles: Effects of NH Protective Groups and Ring Size" by Ishihara, Yugi et al., J. Chem. Soc., Perkin Trans. 1, pp. 3401–3406, 1992.

S.P. Adams et al., "Synthesis, Conformation, and Complexation Behavior of 2,9,18,25–Tetraoxa[8,8] (1,4) napthalenophane", J. Org. Chem. 1981, 46, pp 3474–3478.

*Organic Synthesis*, vol. 31, John Wiley and Sons, Inc., pp 90–92 (1951).

*Organic Synthesis*, vol. 32, John Wiley and Sons, Inc., pp 72–76 (1952).

* cited by examiner

*Primary Examiner*—Deborah C. Lambkin
(74) *Attorney, Agent, or Firm*—Frank P. Mallak

(57) ABSTRACT

Described are novel reversible photochromic naphthopyran compounds, examples of which are compounds having a cycloalkyl ester substituent at the number 5 carbon atom and optionally certain substituents at the number 6 carbon atom of the naphtho portion of the naphthopyran and certain substituents at the 2-position of the pyran ring. Substituents may also be present at the number 7, 8, 9 or 10 carbon atoms of the naphtho portion of the naphthopyran. These compounds may be represented by the following graphic formulae:

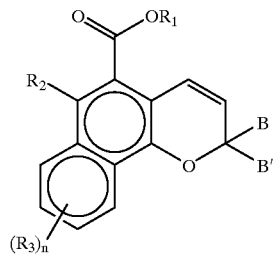

Also described are various substrates, e.g., paper, glass, organic polymeric materials, etc., that contain or that are coated with such compounds. Optically clear articles such as ophthalmic lenses or other plastic transparencies that incorporate the novel naphthopyran compounds or combinations thereof with complementary photochromic compounds, e.g., certain other naphthopyrans, indenonaphthopyrans, benzopyrans, oxazine-type compounds, etc., are also described.

22 Claims, No Drawings

SUBSTITUTED NAPTHOPYRANS

CROSS REFERENCE TO RELATED APPLICATIONS

This application claims priority to provisional application No. 60/175,640, filed on Jan. 12, 2000.

DESCRIPTION OF THE INVENTION

The present invention relates to substituted 2H-naphtho[1,2-b]pyran compounds and to compositions and articles containing such naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion.

U.S. Pat. Nos. 5,458,814, 5,573,712, 5,650,098, 5,656,206 and 5,658,500 disclose 2H-naphtho[1,2-b]pyrans substituted in the 5- and 6-positions that possess a reasonable rate of fade as well as high colorability. The compounds exhibit activated colors ranging from yellow to red/purple. International Patent Application Publication No. WO 98/04937 describes 2H-naphtho[1,2-b]pyrans having alkoxy groups as substituents at the 7- or 9-positions of the naphthopyran ring.

Photochromic compounds may be incorporated into plastic substrates, such as ophthalmic lenses, by various methods described in the art. Such methods include dissolving or dispersing the compound within the surface of a substrate, e.g., imbibition of the photochromic compound into the substrate by immersion of the substrate in a hot solution of the photochromic compound or by depositing the photochromic compound on the surface of the substrate and thermally transferring the photochromic compound from a carrier into the substrate. The term "imbibition" or "imbibe" is intended to mean and include permeation of the photochromic compound into the substrate, solvent assisted transfer absorption of the photochromic compound into the substrate, vapor phase transfer and other such transfer mechanisms.

The extent to which the photochromic compounds penetrate the polymeric substrate generally increases with increasing temperature, increasing concentration of photochromic compounds at the surface of the polymeric substrate and increasing period of contact with the polymeric substrate. The ease with which the photochromic compounds are incorporated is also dependent upon the characteristics of the photochromic compounds and of the polymeric substrate. The molecular size, melting point, and carrier matrix solubility of the photochromic compounds as well as the receptivity of the polymeric substrate all affect the ease of incorporation of the photochromic compounds.

In some cases, due to the numerous variables affecting production of photochromic articles, photochromic compounds may not be incorporated into the plastic substrate with sufficient uniformity and to a sufficient depth. This can result in poor performance of the photochromic compound, e.g., inadequate reversible color change of the photochromic article and non-neutral color formation. Depending on the solubility of the photochromic compound in the inbibition composition, crystals may form and cause cosmetic defects on the surface of the photochromic article.

Methods for incorporating photochromic compounds into polymeric substrates have been disclosed in U.S. Pat. Nos. 4,286,957, 4,880,667, 5,789,015 and 5,975,696. Various photochromic compositions used in the process of incorporating photochromic compounds into polymeric substrates have been disclosed in U.S. Pat. Nos. 5,185,390, 5,391,327 and 5,770,115. As disclosed in U.S. Pat. No. 5,753,146, in order to achieve activated neutral colors, it is necessary to select and combine photochromic naphthopyran compounds on the basis of their lambda max value, sensitivity, optical density and fade rate under solar simulated conditions.

It has been unexpectedly discovered that 2H-naphtho[1,2-b]pyran compounds having a cycloalkyl ester-substituent in the 5-position are more soluble in polymeric matrices used in imbibition processes than 2H-naphtho[1,2-b]pyrans having similar photochromic properties that are substituted with a non-cycloalkyl ester. The cycloalkyl ester-substituted 2H-naphtho[1,2-b]pyran compounds may be used individually or in combination with other complementary photochromic compounds to produce photochromic articles. When used in place of non-cycloalkyl ester-substituted 2H-naphtho[1,2-b]pyran compounds in imbibition processes with polymeric carriers, e.g., hydroxypropyl cellulose, use of the compounds of the present invention enables the successful preparation of photochromic imbibed lenses of neutral activated colors having a reduced occurrence of cosmetic defects.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that 2H-naphtho[1,2-b]pyrans having a cycloalkyl ester substituent at the 5-position may be prepared. These naphthopyran compounds demonstrate improved solubility in polymeric matrices used as carriers in imbibition processes. Use of the compounds of the present invention in place of non-cycloalkyl ester-substituted 2H-naphtho[1,2-b]pyrans in imbibition processes makes possible the preparation of photochromic articles of neutral color having a reduced occurrence of cosmetic defects.

The types of cosmetic defects that can occur on the polymer surface during the imbibition process from the use of a photochromic compound that is not compatible, e.g., soluble, in the imbibition composition include pits, dimples, spots, orange peel, uneven patterns and distortions of reflected light. The terms used to describe these cosmetic defects are also used to describe defects in coatings. Definitions of these and other such surface defect terms are found in the *Paint/Coating Dictionary* by the Federation of Societies for Coating Technology, Philadelphia.

In one contemplated embodiment, photochromic articles prepared by the imbibition of photochromic compounds of the present invention into polymeric organic substrates have a negligible occurrence of cosmetic defects. By the term negligible, it is meant that the number of cosmetic defects is so small and of so little consequence as to warrant little or no attention.

The compounds of the present invention may be described as naphthopyrans having substituents at the 2 position of the pyran ring, at the number 5 position and optionally at the 6 carbon atoms of the naphtho-portion of the naphthopyran ring. Substituents may also be present at the 7, 8, 9 or 10 carbon atoms of the naphtho portion of the naphthopyran ring. These compounds may be represented by the following graphic formula I in which the internal numbers 1 through 10 identify the ring atoms of the naphthopyran:

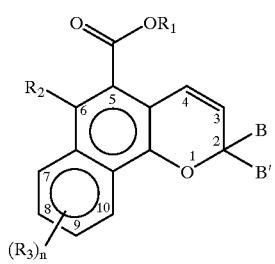

I

In graphic formula I, $R_1$ is $C_3-C_{12}$ cycloalkyl, e.g., cyclopropyl, cyclobutyl, cyclopentyl, cyclohexyl, cycloheptyl, cyclooctyl, cyclononyl, cyclodecyl, cycloundecyl and cyclododecyl; mono($C_1-C_6$)alkyl substituted $C_3-C_{12}$ cycloalkyl, e.g., methylcyclopropyl, ethylcyclopentyl, propylcyclohexyl, etc.; mono($C_1-C_6$) alkoxy substituted $C_3-C_{12}$ cycloalkyl, halo($C_3-C_{12}$) cycloalkyl; $C_4-C_{12}$ bicycloalkyl, e.g., bicyclo[2.2.1]heptyl (norbornyl), 1,7,7-trimethyl bicyclo[2.2.1]heptyl (bornyl), bicyclo[3.2.1]octyl, bicyclo[3.3.1]nonan-9-yl and bicyclo[4.3.2]undecyl; or $C_7-C_{12}$ tricycloalkyl, e.g., tricyclo[2.2.1.0$^{2,6}$]heptyl, tricyclo[3.3.1.1$^{3,7}$]decyl (adamantyl), and tricyclo[5.3.1.1$^{2,6}$]dodecyl. The halo substituents are bromo, chloro, fluoro or iodo.

In one contemplated embodiment, $R_1$ is $C_3-C_{10}$ cycloalkyl, mono($C_1-C_3$)alkyl substituted $C_3-C_{10}$ cycloalkyl, mono($C_1-C_3$)alkoxy substituted $C_3-C_{10}$ cycloalkyl, halo($C_3-C_{10}$) cycloalkyl, $C_7-C_{10}$ bicycloalkyl or $C_7-C_{10}$ tricycloalkyl, wherein the halo substituents are chloro or fluoro. In another contemplated embodiment, $R_1$ is $C_3-C_7$ cycloalkyl.

$R_2$ in graphic formula I may be hydrogen, $C_1-C_6$ alkyl, $C_3-C_7$ cycloalkyl, phenyl, mono-, di- or tri-substituted phenyl, the group —$OR_4$, wherein $R_4$ is hydrogen, $C_1-C_6$ alkyl, phenyl($C_1-C_3$)alkyl, mono($C_1-C_6$)alkyl substituted phenyl($C_1-C_3$)alkyl, mono($C_1-C_6$)alkoxy substituted phenyl($C_1-C_3$)alkyl, ($C_1-C_6$)alkoxy($C_2-C_4$)alkyl, $C_3-C_7$ cycloalkyl, mono($C_1-C_4$)alkyl substituted $C_3-C_7$ cycloalkyl, $C_1-C_6$ haloalkyl, allyl or the group, —$CH(R_5)X$, wherein X is CN, $CF_3$, halogen or —$C(O)W$ wherein W is —$OR_9$ or —$N(R_{10})R_{11}$, $R_5$ is hydrogen or $C_1-C_6$ alkyl, $R_9$ is hydrogen, allyl, $C_1-C_6$ alkyl, phenyl, mono($C_1-C_6$)alkyl substituted phenyl, mono($C_1-C_6$)alkoxy substituted phenyl, phenyl($C_1-C_3$)alkyl, mono($C_1-C_6$)alkyl substituted phenyl ($C_1-C_3$)alkyl, mono($C_1-C_6$)alkoxy substituted phenyl ($C_1-C_3$)alkyl, $C_1-C_6$ alkoxy($C_2-C_4$)alkyl, $C_1-C_6$ haloalkyl or $R_1$, and $R_{10}$ and $R_{11}$ are each selected from the group consisting of hydrogen, $C_1-C_6$ alkyl, $C_3-C_7$ cycloalkyl, phenyl, mono-substituted phenyl and di-substituted phenyl; or $R_4$ is the group, —$C(O)Y$, wherein Y is hydrogen, $C_1-C_6$ alkyl, $C_1-C_6$ alkoxy, the mono- or di-substituted or unsubstituted aryl groups phenyl or naphthyl, phenoxy, $C_1-C_6$ mono- or di-alkyl substituted phenoxy, $C_1-C_6$ mono- or di-alkoxy substituted phenoxy, $C_1-C_6$ alkylamino, phenylamino, $C_1-C_6$ mono- or di-alkyl substituted phenylamino, or $C_1-C_6$ mono- or di-alkoxy substituted phenylamino, each of said aryl, i.e., phenyl or naphthyl, substituents being selected from $C_1-C_6$ alkyl or $C_1-C_6$ alkoxy, each of said halogen or halo substituents are bromo, chloro, fluoro or iodo.

In one contemplated embodiment, $R_2$ is hydrogen, $C_1-C_3$ alkyl, $C_3-C_5$ cycloalkyl, phenyl, mono- or di-substituted phenyl or —$OR_4$, wherein $R_4$ is hydrogen, $C_1-C_3$ alkyl, or the group, —$CH(R_5)X$, wherein X is CN or —$C(O)W$ wherein W is —$OR_9$ or —$N(R_{10})R_{11}$, $R_5$ is hydrogen or methyl, $R_9$ is hydrogen, $C_1-C_4$ alkyl, phenyl, mono($C_1-C_4$) alkyl substituted phenyl, mono($C_1-C_4$)alkoxy substituted phenyl, phenyl($C_1-C_2$)alkyl, mono($C_1-C_4$)alkyl substituted phenyl($C_1-C_2$)alkyl, mono($C_1-C_4$)alkoxy($C_2-C_3$)alkyl, $C_1-C_4$ haloalkyl or $R_1$, and $R_{10}$ and $R_{11}$ are each selected from the group consisting of hydrogen, $C_1-C_4$ alkyl, $C_5-C_7$ cycloalkyl, phenyl, mono-substituted phenyl and di-substituted phenyl; or $R_4$ is the group —$C(O)Y$ wherein Y is $C_1$–$C_3$ alkyl or $C_1$–$C_3$ alkoxy, each of said phenyl substituents being $C_1$–$C_3$ alkyl or $C_1$–$C_3$ alkoxy, and each of said halo substituents are chloro or fluoro. In another contemplated embodiment, $R_2$ is hydrogen or $C_1$–$C_3$ alkyl.

Each $R_3$ in graphic formula I may be independently selected from the aforementioned substituents assigned to $R_2$, and n is selected from the integers 0, 1, 2, and 3. In one contemplated embodiment, each $R_3$ is hydrogen, $C_1$–$C_4$ alkyl, $C_3$–$C_{10}$ cycloalkyl, phenyl, mono- or di- substituted phenyl, said phenyl substituents being $C_1$–$C_3$ alkyl or $C_1$–$C_3$ alkoxy, and n is the integer 0, 1 or 2. In another contemplated embodiment, $R_3$ is hydrogen or $C_1$–$C_3$ alkyl and n is 0 or 1.

In the definitions of $R_1$, $R_2$ and $R_3$ in graphic formula I, like letters have the same meaning unless stated otherwise. The carbon ranges disclosed for the substituents herein were selected on the basis of commercial availability. Compounds of the present invention may have substituents having carbon ranges outside of those listed as such materials become available.

B and B' may each be selected from the group consisting of:

(a) the unsubstituted, mono-, di- and tri-substituted aryl groups, phenyl and naphthyl;

(b) 9-julolidinyl and the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (a) and (b) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, haloaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl ($C_1$–$C_6$)alkyl, mono- and di-($C_1$–$C_6$)alkoxyaryl ($C_1$–$C_6$)alkyl, mono- and di-($C_1$–$C_6$)alkylaryl($C_1$–$C_6$) alkoxy, mono- and di-($C_1$–$C_6$)alkoxyaryl($C_1$–$C_6$) alkoxy, amino, mono($C_1$–$C_6$)alkylamino, di($C_1$–$C_6$) alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ haloalkyl, $C_1$–$C_6$ alkoxy, mono ($C_1$–$C_6$)alkoxy($C_1$–$C_4$)alkyl, acryloxy, methacryloxy, and halogen, said halo and halogen being bromo, chloro, fluoro or iodo; each aryl, either alone or as a component of a substituent, e.g., haloaryl, aryloxy, etc., described for the aryl and heteroaromatic substituents in parts (a) and (b) is phenyl or naphthyl;

(c) the unsubstituted or mono-substituted groups, pyrazolyl, imidazolyl, pyridyl, pyrazolinyl, imidazolinyl, pyrrolinyl, phenothiazinyl, phenoxazinyl, phenazinyl or acridinyl, each of said substituents for said groups in part (c) being selected from the group consisting of $C_1$–$C_6$ alkyl, $C_1$–$C_6$ alkoxy, phenyl and halogen, as defined in part (b);

(d) monosubstituted phenyl, having a substituent at the para position that is the linking group, —(CH$_2$)$_t$— or —O—(CH$_2$)$_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran;

(e) the group represented by the following graphic formula IIA or IIB:

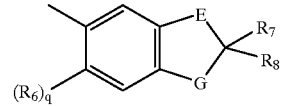

IIA

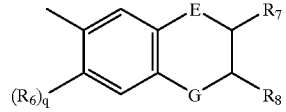

IIB wherein E is methylene or oxygen and G is oxygen or substituted nitrogen, provided that when G is substituted nitrogen, E is methylene, said nitrogen substituents being selected from the group consisting of hydrogen, $C_1$–$C_6$ alkyl and $C_2$–$C_6$ acyl; each $R_6$ is $C_1$–$C_6$ alkyl, $C_1$–$C_6$ alkoxy, hydroxy, halogen; $R_7$ and $R_8$ are each hydrogen or $C_1$–$C_6$ alkyl; and q is the integer 0, 1 or 2;

(f) $C_1$–$C_6$ alkyl, $C_1$–$C_6$ haloalkyl, $C_1$–$C_6$ alkoxy($C_1$–$C_4$) alkyl, $C_3$–$C_{12}$)cycloalkyl, mono($C_1$–$C_6$)alkoxy ($C_3$–$C_{12}$)cycloalkyl, mono($C_1$–$C_6$)alkyl($C_3$–$C_{12}$)-cycloalkyl, halo($C_3$–$C_{12}$)cycloalkyl and $C_4$–$C_{12}$ bicycloalkyl, said halo being bromo, chloro, fluoro or iodo; and (g) the group represented by the following graphic formula IIC:

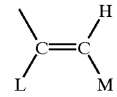

IIC wherein L is hydrogen or $C_1$–$C_4$ alkyl and M is selected from the unsubstituted, mono-, and di-substituted members of the group consisting of naphthyl, phenyl, furanyl and thienyl, each of said group substituents in (g) being $C_1$–$C_4$ alkyl, $C_1$–$C_4$ alkoxy or halogen.

Alternatively, B and B' taken together may form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, and cyclododecylidene; saturated $C_4$–$C_{12}$ spiro-bicyclic hydrocarbon rings, e.g., bicyclo[2.2.1]heptylidene (norbornylidene), 1,7,7-trimethyl bicyclo[2.2.1]heptylidene (bornylidene), bicyclo[3.2.1]octylidene, bicyclo[3.3.1] nonan-9-ylidene, bicyclo[4.3.2]undecane, and saturated $C_7$–$C_{12}$ spiro-tricyclic hydrocarbon rings, e.g., tricyclo [2.2.1.0$^{2,6}$]heptylidene, tricyclo[3.3.1.1$^{3,7}$]decylidene (adamantylidene), and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy and halogen.

In one contemplated embodiment, B and B' are each selected from the group consisting of:

(a) phenyl, mono-substituted and di-substituted phenyl;

(b) the unsubstituted, mono- and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in parts (a) and (b) being selected from the group consisting of hydroxy, aryl, aryloxy, aryl($C_1$–$C_3$)alkyl, amino, mono($C_1$–$C_3$)alkylamino, di($C_1$–$C_3$) alkylamino, N-($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, chloro and fluoro;

(c) the groups represented by graphic formulae IIA and IIB wherein E is methylene and G is oxygen, $R_6$ is $C_1$–$C_3$ alkyl or $C_1$–$C_3$ alkoxy; $R_7$ and $R_8$ are each hydrogen or $C_1$–$C_4$ alkyl; and q is 0 or 1;

(d) $C_1$–$C_4$ alkyl; and (e) the group represented by graphic formula IIC, wherein L is hydrogen or methyl and M is phenyl or mono-substituted phenyl, said phenyl substituent being $C_1$–$C_3$ alkyl, $C_1$–$C_3$ alkoxy or fluoro; or B and B' taken together form fluoren-9-ylidene, mono-substituted fluoren-9-ylidene or a member selected from the group consisting of saturated $C_3$–$C_{10}$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

In another contemplated embodiment, B and B' are each selected from the group consisting of:

(a) phenyl, mono- and di-substituted phenyl, preferably substituted in the meta and/or para positions;

(b) the unsubstituted, mono- and di-substituted heteroaromatic groups furanyl, benzofuran-2-yl, thienyl and benzothien-2-yl, each of said phenyl and heteroaromatic substituents in (a) and (b) being selected from the group consisting of hydroxy, $C_1$–$C_3$ alkyl, $C_1$–$C_3$ alkoxy, phenyl, indolino, fluoro and chloro;

(c) the group represented by graphic formulae IIA wherein E is methylene and G is oxygen, $R_6$ is $C_1$–$C_3$ alkyl or $C_1$–$C_3$ alkoxy; $R_7$ and $R_8$ are each hydrogen or $C_1$–$C_3$ alkyl; and q is 0 or 1; or B and B' taken together form fluoren-9-ylidene, adamantylidene, bornylidene, norbornylidene, or bicyclo[3.3.1]nonan-9-ylidene.

Compounds represented by graphic formula I may be prepared by the following steps. In Reaction A, compounds represented by graphic formula V or VA are either purchased or prepared by Friedel-Crafts methods using an appropriately substituted or unsubstituted benzoyl chloride of graphic formula IV with a commercially available substituted or unsubstituted benzene compound of graphic formula III. See the publication *Friedel-Crafts and Related Reactions,* George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent potential phenyl substituents.

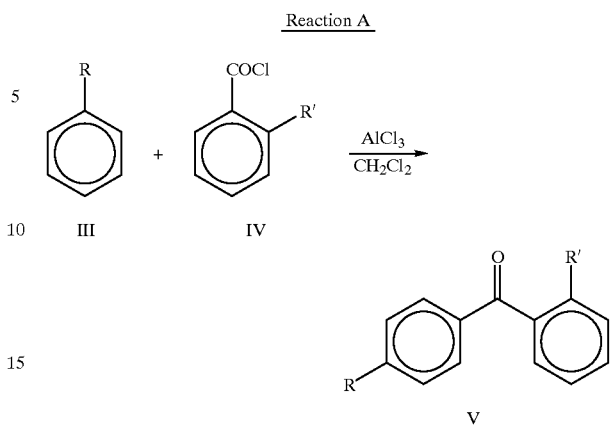

Reaction A

In Reaction B, the substituted or unsubstituted ketone is represented by graphic formula VA, in which B and B' may represent groups other than substituted or unsubstituted phenyl, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound. Propargyl alcohols having a B or B' group represented by graphic formula IIC may be prepared by the methods described in U.S. Pat. No. 5,274,132, column 2, lines 40 to 68.

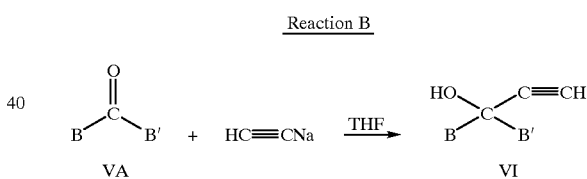

Reaction B

In Reaction C, a method for making the compounds represented by graphic formula XI that may not be commercially available is disclosed. A substituted or unsubstituted acetophenone, benzophenone, or benzaldehyde represented by graphic formula VII is reacted with dimethyl succinate (graphic formula VIII) in the presence of a base such as sodium hydride or a potassium t-butoxide in a suitable solvent such as toluene to form the appropriate substituted monoester of an a-arylidene succinic acid, represented by graphic formula IX. Other substituents on the compound represented by graphic formula IX may be prepared by using different succinate esters, such as diethyl succinate. Compound IX is heated with acetic anhydride and anhydrous sodium acetate to form the corresponding acetate derivative represented by the graphic formula X. Compound X is reacted with potassium hydroxide in an aqueous alcohol mixture such as ethanol in water to form the corresponding substituted naphthoic acid, represented by graphic formula XI. Reaction C is further described in the text *Organic Reactions,* Vol. VI, Chapter 1, pages 1–73, John Wiley & Sons, Inc., New York.

Reaction C

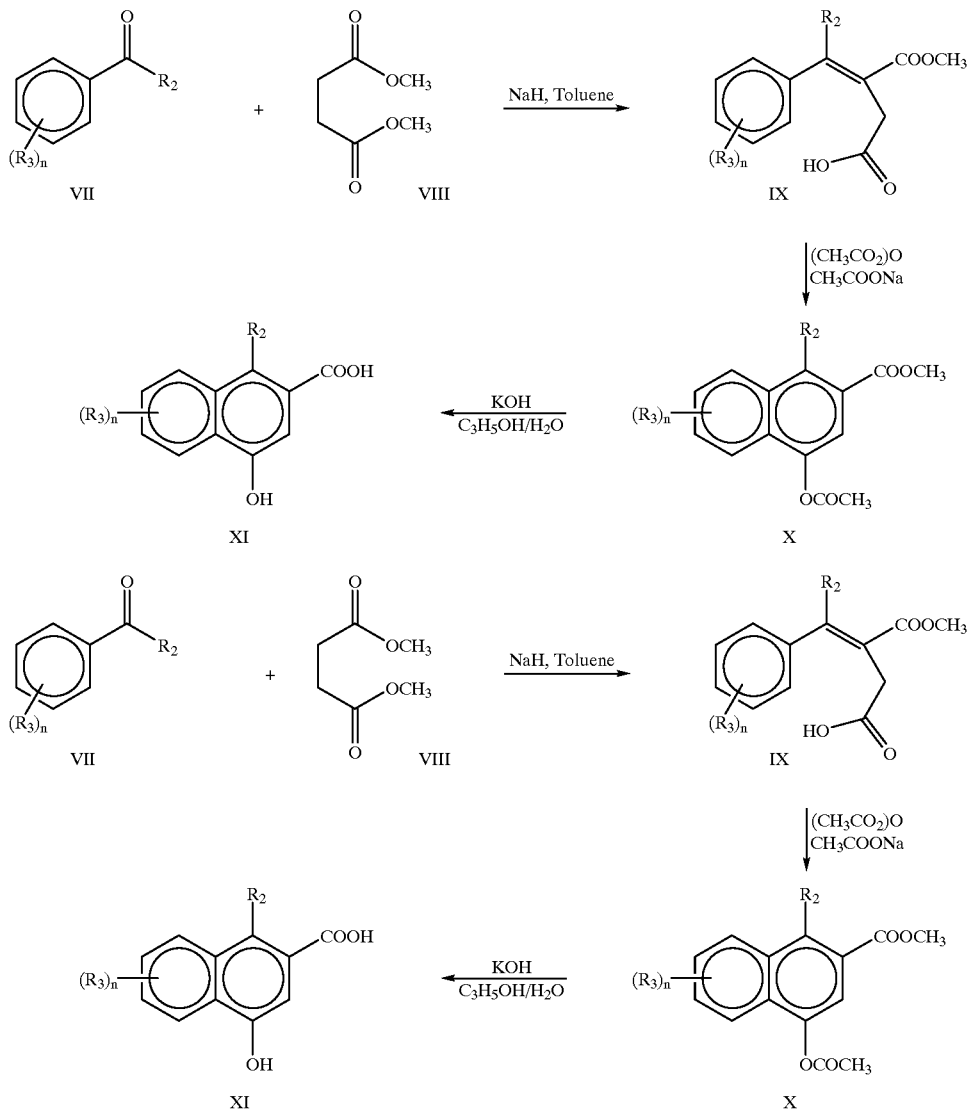

In Reaction D, 4-hydroxy-2-naphthoic acid substituted with $(R_3)_n$ and $R_2$ at the 1-position, represented by graphic formula XI, is reacted with $R_1$-halide, e.g., cyclohexyl iodide, in the presence of potassium carbonate in a suitable solvent such as anhydrous dimethylformamide (DMF), to form the corresponding 4-hydroxy-2-naphthoate substituted with $(R_3)_n$ and $R_2$ at the 1-position, which is represented by graphic formula XII. This reaction is further described in The Journal of Organic Chemistry, 46(17), 1981, page 3477. The compound represented by graphic formula XI may be prepared by following the scheme of Reaction C disclosed in U.S. Pat. No. 6,106,744.

Reaction D

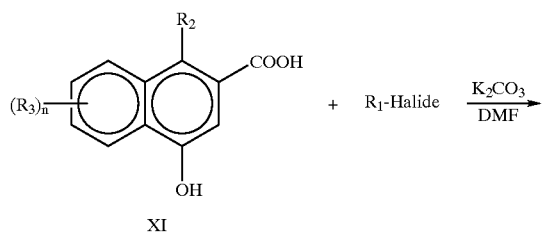

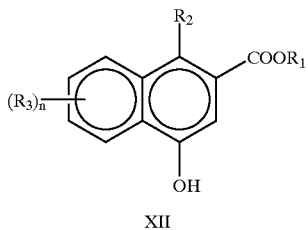

XII

In Reaction E, the propargyl alcohol represented by graphic formula VI is coupled with the naphthol represented by graphic formula XIA (which represents the same compounds as graphic formula VIII except that the bonding of the substituent at the 2-position is shown) to form compounds represented by graphic formula I.

Reaction E

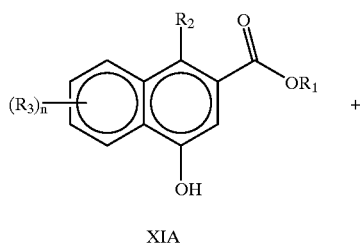

XIA

+

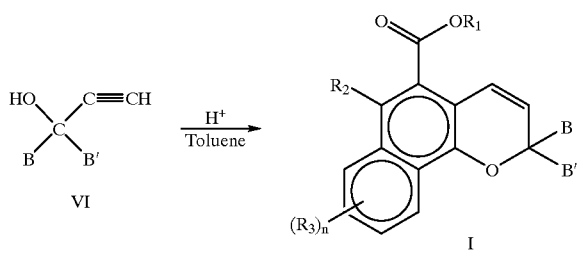

As shown in Reaction F, when $R_2$ in graphic formula I is —OH, this substituent can be converted to a variety of different groups by reacting such compounds, as represented by graphic formula IA, with acylating or alkylating agents. For example, Compound IA may be reacted with methyl iodide (or other alkylating agent) in the presence of anhydrous potassium carbonate in a suitable solvent such as anhydrous acetone to form compounds represented by graphic formula IB, in which $R_2$ is a methoxy substituent. Alkylating reactions are further described in "Organic Synthesis," Vol. 31, pages 90–93, John Wiley & Sons, Inc., New York, N.Y. Alternatively, Compound IA may be reacted with acetyl chloride (or other acylating agent) in the presence of triethylamine in an appropriate solvent, such as methylene chloride, to form compounds represented by the graphic formula IC, in which $R_2$ is an acetoxy substitutent. Acylating reactions are further described in "Organic Synthesis," Vol. 32, pages 72–77, John Wiley & Sons, Inc., New York, N.Y.

Reaction F

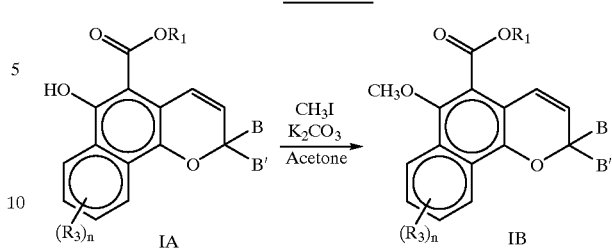

Compounds represented by graphic formula I may be used in those applications in which organic photochromic substances may be employed, such as optical lenses, e.g., vision correcting ophthalmic lenses, contact lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions. As used herein, coating compositions are defined herein to include polymeric coating compositions prepared from materials such as polyurethanes, epoxy resins and other resins used to produce synthetic polymers; paints, i.e., a pigmented liquid or paste used for the decoration, protection and/or the identification of a substrate; and inks, i.e., a pigmented liquid or paste used for writing and printing on substrates. Potential substrates for coating compositions containing the compounds of the present invention include paper, glass, ceramics, wood, masonry, textiles, metals and polymeric organic materials.

Coating compositions may be used to produce coatings on optical elements, verification marks on security documents, e.g., documents such as banknotes, passport and drivers' licenses, for which authentication or verification of authenticity may be desired. The 2H-naphtho-[1,2-b]pyrans represented by graphic formula I exhibit color changes from colorless to colors ranging from yellow to red/purple.

Examples of naphthopyrans and contemplated naphthopyrans that have or are expected to have desirable photochromic properties and that are within the scope of the invention are the following:

(a) 2,2-Diphenyl-5-cyclohexyloxycarbonyl-8-methyl-[2H]-naphtho[1,2-b]pyran;
(b) 2,2-Bis(4-methoxyphenyl)-5-cyclopropyloxycarbonyl-6-methoxy-[2H]-naphtho[1,2-b]pyran;
(c) 2,2-Bis(4-methoxyphenyl)-5-cyclooctyloxycarbonyl-6-(ethoxycarbonyl)methoxy-[2H]-naphtho[1,2-b]pyran;

(d) 2,2-Bis(4-methylphenyl)-5-cyclohexyloxycarbonyl-6-(methoxycarbonyloxy)-[2H]-naphtho[1,2-b]pyran;
(e) 2,2-Diphenyl-5-cyclopropyloxycarbonyl-6-acetoxy-[2H]-naphtho[1,2-b]pyran;
(f) 2,2-Bis(4-methoxyphenyl)-5-cyclooctyloxycarbonyl-6-methyl-[2H]-naphtho[1,2-b]pyran;
(g) 2,2-Bis(4-methoxyphenyl)-5-cycloheptyloxycarbonyl-6-methyl-9-methoxy-[2H]-naphtho[1,2-b]pyran;
(h) 2-(4-Methoxyphenyl)-2-(2-methyl,2,3-dihydrobenzofuran-5-yl)-5-cyclobutyloxycarbonyl-6-(ethoxycarbonyl)methoxy-[2H]-naphtho[1,2-b]pyran;
(i) 2-phenyl-2-(2-dibenzofuryl)-5-cyclohexyloxycarbonyl-8-methyl-[2H]-naphtho[1,2-b]pyran;
(j) 2,2-diphenyl-5-cyclohexyloxycarbonyl-8-methoxy-[2H]-naphtho[1,2-b]pyran;
(k) 2-phenyl-2-(4-methoxyphenyl)-5-cyclohexyloxycarbonyl-8-methoxy-[2H]-naphtho[1,2-b]pyran; and
(1) 2-phenyl-2-(4-methylphenyl)-5-cyclohexyloxycarbonyl-8-methoxy-[2H]-naphtho[1,2-b]pyran.

Other than in the operating examples, or where otherwise indicated, all numbers expressing wavelengths, quantities of ingredients or reaction conditions used herein are to be understood as modified in all instances by the term "about".

The disclosures of the patents and articles cited herein describing photochromic imbibition processes and compositions, procedures for making the compounds of the present invention, complementary photochromic compounds, polymeric coatings and methods of applying such coatings, polymeric organic host materials and polymerizates are incorporated herein, in toto, by reference.

It is contemplated that the photochromic naphthopyrans of the present invention may each be used alone or in combination with other naphthopyrans of the present invention. Alternatively, the photochromic naphthopyrans of the present invention may be used in combination with one or more other appropriate complementary organic photochromic materials, i.e., organic photochromic compounds having at least one activated absorption maxima within the range of between 400 and 700 nanometers, or substances containing the same. The photochromic compounds may be incorporated, e.g., dissolved or dispersed, in a polymeric organic host material used to prepare photochromic articles which color when activated to an appropriate hue.

The complementary organic photochromic materials may include other naphthopyrans, benzopyrans, indenonaphthopyrans, phenanthorpyrans, spiro (benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro (indoline)pyridobenzoxazines, spiro(benzindoline) pyridobenzoxazines, spiro(benzindoline)naphthoxazines, spiro(indoline)benzoxazines, mercury dithizonates, fulgides, fulgimides and mixtures of such photochromic compounds. Such photochromic compounds are described in U.S. Pat. Nos. 5,645,767 and 6,153,126.

The photochromic compounds of the present invention may be associated with a polymeric organic host material or other substrate by various means. They may be incorporated, i.e., dissolved and/or dispersed, into the host material, polymerized with other components of the host material, and/or incorporated into a coating applied to a substrate, e.g., a polymeric coating applied to one surface of the polymeric organic host material.

Each of the photochromic substances described herein may be used in amounts (or in a ratio) such that an organic host material or substrate to which the photochromic compounds or mixture of compounds is associated, exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe colors may be found in U.S. Pat. No. 5,645,767 column 12, line 66 to column 13, line 19.

The amount of the photochromic naphthopyrans to be applied to or incorporated into a coating composition or host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic compounds. Typically, the more photochromic compound applied or incorporated, the greater is the color intensity up to a certain limit.

The relative amounts of the aforesaid photochromic compounds used will vary and depend in part upon the relative intensities of the color of the activated species of such compounds, the ultimate color desired and the method of application to the host material or substrate. Generally, the amount of total photochromic compound incorporated into or applied to a photochromic optical host material may range from 0.05 to 2.0, e.g., from 0.2 to 1.0, milligrams per square centimeter of surface to which the photochromic compound is incorporated or applied. The amount of photochromic material incorporated into a coating composition may range from 0.1 to 40 weight percent based on the weight of the liquid coating composition.

The photochromic naphthopyrans of the present invention may be associated with the host material by various methods described in the art. See, for example, column 13, lines 40 to 58 of U.S. Pat. No. 5,645,767. Aqueous or organic solutions or dispersions of the photochromic compounds may be used to incorporate the photochromic compounds into a polymeric organic host material or other materials such as textiles and coating compositions. Coating compositions may be applied to the substrate using a coating process such as that described in U.S. Pat. No. 3,971,872.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays.

The polymeric coating composition includes compositions resulting in thermoplastic or thermosetting coatings, which are described in the *Kirk-Othmer Encyclopedia of Chemical Technology,* Fourth Edition, Volume 6, pages 669 to 760. The coating may comprise at least one polymer selected from the group consisting of polyurethanes, melamine resins, polyvinyl alcohol, polyacrylates, polymethacrylates, polyamide resins and epoxy resins. Such polymer-forming coating compositions are described in U.S. Pat. No. 4,425,403.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Most preferably, the polymeric organic host material is a solid transparent or optically clear material, e.g., materials suitable for optical applications, such as plano, ophthalmic and contact lenses, windows, automotive transparencies, e.g., windshields, aircraft transparencies, plastic sheeting, polymeric films, etc.

Examples of polymeric organic host materials which may be used with the photochromic compounds described herein include: polymers, i.e., homopolymers and copolymers, of the bis(allyl carbonate) monomers, diethylene glycol dimethacrylate monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, mono- or polyfunctional, e.g., di- or multi-functional, acrylate and/or methacrylate monomers, poly($C_1$–$C_{12}$ alkyl methacrylates), such as poly(methyl methacrylate), poly(oxyalkylene)dimethacrylate, poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polythiourethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No. 5,753,146, column 8, line 62 to column 10, line 34.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly contemplated is use of the photochromic naphthopyrans of the present invention with optical organic resin monomers used to produce optically clear coatings and polymerizates, i.e., materials suitable for optical applications, such as for example plano and ophthalmic lenses, windows, and automotive transparencies. Such optically clear polymerizates may have a refractive index that may range from 1.48 to 1.75, e.g., from 1.495 to 1.66.

Specifically contemplated are polymerizates of optical resins sold by PPG Industries, Inc. under the CR-designation, e.g., CR-307, CR-407 and CR-607, and polymerizates prepared for use as hard or soft contact lenses. Methods for producing both types of contact lenses are disclosed in U.S. Pat. No. 5,166,345, column 11, line 52, to column 12, line 52. Additional polymerizates contemplated for use with the photochromic naphthopyrans of the present invention are polymerizates used to form soft contact lenses with high moisture content described in U.S. Pat. No. 5,965,630 and extended wear contact lenses described in U.S. Pat. No. 5,965,631.

The present invention is more particularly described in the following examples, which are intended as illustrative only, since numerous modifications and variations therein will be apparent to those skilled in the art.

EXAMPLE 1

Step 1

7-Methyl-4-hydroxy-2-naphthoic acid (25 grams), cyclohexyl iodide (27.3 grams) and potassium carbonate (50 grams) were added to a reaction flask containing 200 milliliters (mL) of dimethylformamide and heated to reflux. After maintaining the reflux temperature for 18 hours, the contents of the reaction flask was added to a beaker containing 500 mL of a mixture of ice and water. The resulting mixture was extracted three times with diethyl ether (100 mL) each time. The recovered product, 3 grams, had a nuclear magnetic resonance (NMR) spectrum which showed the product to have a structure consistent with 7-methyl-4-hydroxy-2-cyclohexyloxycarbonyl naphthalene.

Step 2

7-Methyl-4-hydroxy-2-cyclohexyloxycarbonyl naphthalene (3 grams) from Step 1 and 1,1-diphenyl-2-propyn-1-ol (2.5 grams) were added to a reaction flask (equipped with a magnetic stirrer, Stark trap and condenser) containing 100 mL of chloroform and stirred. A catalytic amount of p-toluenesulfonic acid (about 100 milligrams) was added, and the mixture was heated to reflux and stirred for 2 hours. Afterwards, the reaction mixture was washed with water and the remaining solvent was removed under vacuum. The resulting residue was purified using a silica gel column and 15 weight percent ethylacetate in hexane as the eluant. The photochromic fractions were combined and the solvent was removed under vacuum. The resulting product was induced to crystallize from a 1:1 toluene/ether mixture to yield 1.5 grams of bright yellow crystals. The recovered product had a melting point of 188–189° C. A nuclear magnetic resonance (NMR) spectrum showed the product to have a structure consistent with 2,2-diphenyl-5-cyclohexyloxycarbonyl-8-methyl-[2H]-naphtho[1,2-b] pyran.

EXAMPLE 2

The procedure of Example 1 was followed except that in Step 2, 1-phenyl-1-(2-dibenzofuryl)-2-propyn-1-ol was used in place of 1,1-diphenyl-2-propyn-1-ol. The NMR spectrum showed the structure to be consistent with 2-phenyl-2-(2-dibenzofuryl)-5-cyclohexyloxycarbonyl-8-methyl-[2H]-naphtho[1,2-b]pyran.

EXAMPLE 3

The procedure of Example 1 was followed except that in Step 2, 7-methoxy-4-hydroxy-2-cyclohexyloxycarbonyl naphthalene was used in place of 7-methyl-4-hydroxy-2-cyclohexyloxycarbonyl naphthalene. The NMR spectrum showed the structure to be consistent with 2,2-diphenyl-5-cyclohexyloxycarbonyl-8-methoxy-[2H]-naphtho[1,2-b] pyran.

EXAMPLE 4

The procedure of Example 1 was followed except that in Step 2, 7-methoxy-4-hydroxy-2-cyclohexyloxycarbonyl naphthalene was used in place of 7-methyl-4-hydroxy-2-cyclohexyloxycarbonyl naphthalene and 1-phenyl-1-(4-methoxyphenyl)-2-propyn-1-ol was used in place of 1,1-diphenyl-2-propyn-1-ol. The NMR spectrum showed the structure to be consistent with 2-phenyl-2-(4-methoxyphenyl)-5-cyclohexyloxycarbonyl-8-methoxy-[2H]-naphtho[1,2-b]pyran.

EXAMPLE 5

The procedure of Example 1 was followed except that in Step 2, 7-methoxy-4-hydroxy-2-cyclohexyloxycarbonyl naphthalene was used in place of 7-methyl-4-hydroxy-2-cyclohexyloxycarbonyl naphthalene and 1-phenyl-1-(4-methylphenyl)-2-propyn-1-ol was used in place of 1,1-diphenyl-2-propyn-1-ol. The NMR spectrum showed the structure to be consistent with 2-phenyl-2-(4-methylphenyl)-5-cyclohexyloxycarbonyl-8-methoxy-[2H]-naphtho[1,2-b]pyran.

Comparative Examples 1–2

Two 2H-naphthopyrans having non-cycloalkyl ester substituents at the 5 position were prepared following the procedures of U.S. Pat. No. 5,458,814. The compounds of the Comparative Examples were determined to be:

(CE1) 2,2-diphenyl-5-methoxycarbonyl-8-methyl-[2H]-naphtho[1,2-b]pyran; and (CE2) 2,2-diphenyl-5-isopropoxycarbonyl-8-methyl-[2H]-naphtho[1,2-b]pyran.

EXAMPLE 6

Part A

Testing was done with the photochromic compounds described in Examples 1–5 and Comparative Examples (CE) 1 and 2 in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60°C. for 16 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were conditioned, i.e., exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° C. (22.2° C.) The bench was fitted with a 250 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliwatts per square centimeter (mW/$cm^2$). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta OD$) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\%Ta)$, where %Ta is the percent transmittance in the activated state and the logarithm is to the base 10.

The optical properties of the photochromic compound in the test squares are reported in Table 1. The $\Delta OD/Min$, which represents the sensitivity of the photochromic compound's response to UV light, was measured over the first five (5) seconds of UV exposure, then expressed on a per minute basis. The saturation optical density ($\Delta OD@$ Saturation) was taken under identical conditions as the $\Delta OD/Min$, except UV exposure was continued for 15 minutes. The lambda max (Vis) is the wavelength in nanometers (nm) in the visible spectrum at which the maximum absorption of the activated (colored) form of the photochromic compound in a test square occurs. The lambda max (Vis) wavelength was determined by testing the photochromic test square polymerizates of Part A in a Varian Cary 3 UW-Visible spectrophotometer. The Bleach Rate (T 1/2) is the time interval in seconds for the absorbance of the activated form of the photochromic compound in the test squares to reach one half the highest absorbance at room temperature (72° F., 22.2° C.) after removal of the source of activating light.

TABLE 1

| Example Number | (λ) max (VIS) | ΔOD/MIN Sensitivity | ΔOD @ Saturation | Bleach Rate (T ½) |
|---|---|---|---|---|
| 1 | 467 | 0.32 | 0.38 | 72 |
| 2 | 493 | 0.22 | 0.19 | 44 |

TABLE 1-continued

| Example Number | (λ) max (VIS) | ΔOD/MIN Sensitivity | ΔOD @ Saturation | Bleach Rate (T ½) |
|---|---|---|---|---|
| 3 | 460 | 0.40 | 0.52 | 79 |
| 4 | 480 | 0.39 | 0.35 | 45 |
| 5 | 460 | 0.37 | 0.45 | 64 |
| CE1 | 467 | 0.27 | 0.37 | 71 |

The results of Table 1 show that the compounds of the present invention demonstrate a range of photochromic properties, e.g., lambda max values from 460 to 493 nanometers, sensitivity levels from 0.22 to 0.40, values for $\Delta OD$ @ Saturation from 0.19 to 0.52 and Bleach Rates from 44 to 79 seconds. Comparative Examples 1 and 2, having a methyl ester substituent and an isopropyl ester substituent, respectively, at the 5-position of the naphtho portion of the naphthopyran, demonstrate photochromic properties similar to Example 1.

Part C

The following materials were added in the order and the manner described to a container suitable for use with a BRINKMAN PT-3000 homogenizer and mixed by the homogenizer at a speed of 5000 rpm for 2 minutes or until the materials were dissolved.

| Material | Weight (grams) |
|---|---|
| 2-Ethoxy ethyl ether | 30.0 |
| Tetrahydrofurfuryl alcohol | 35.0 |
| n-Methyl pyrrolidone | 20.0 |
| Hydroxypropyl cellulose | 12.0 |
| Silica | 0.9 |

The photochromic compounds of Example 1, Comparative Examples 1 and 2 were individually added with TINUVIN® 144 UV stabilizer, reported to be a hindered amine available from Ciba-Geigy, to 10 ml aliquots of the homogenate to make the imbibition compositions. The weight percent, based on the total weight of the imbibition composition, of the photochromic compound and stabilizer for the two different concentrations tested (A and B) is listed in the following table.

| Material | Conc. A Weight % | Conc. B Weight % |
|---|---|---|
| Photochromic Compound | 2.4 | 4.7 |
| TINUVIN ® 144 UV stabilizer | 1.2 | 2.3 |

Part D

The solutions of Part C for Example 1, Comparative Examples 1 and 2 and stabilizer were imbibed into duplicate sample lenses cast from an optical resin sold by PPG Industries, Inc. under the designation CR-307. This was done by applying the imbibition formulation onto the surface of the test lenses by spin coating. The applied coatings had a clear appearance when wet and became hazy when dry.

The average wet weight of the resin film that formed on the lens ranged from 0.35 to 0.40 grams per lens. The resin film was dried beneath an infrared lamp (Fostoria Sun-mite Model FFH-912 900 Watts) held about 13 inches above -the lenses for 10 to 15 minutes. The lenses were then heated in a hot-air oven at 135–140° C. for 3 hours and one of each pair of duplicate lenses was examined visually. The visual examination was done by moving the coated lens surface from a position parallel to a fluorescent light to a position that is perpendicular while observing any defects in the coating. The fluorescent light was a 34 Watt 4 feet (122 centimeters) long light positioned at a distance of about 6 feet (183 centimeters) above the lens. The appearance of each lens coated with the solutions of concentration A or B samples is described in Table 2. After cooling, the resin film was removed from the other duplicate test samples by rinsing with water and wiping with an acetone soaked tissue. The lenses were examined visually in the same manner as described above. The results of the second visual examination are listed in Table 3.

TABLE 2

| Sample | Appearance of Imbibition Film of Concentration A sample on surface | Appearance of Imbibition Film of Concentration B sample on surface |
| --- | --- | --- |
| Example 1 and stabilizer* | No defects | A few scattered, small, raised crystals |
| Comparative Example 1 and stabilizer* | Numerous scattered, small, raised crystals | Numerous scattered, small, raised crystals and an unevenly coated surface pattern |
| Comparative Example 2 and stabilizer* | Numerous scattered, small, raised crystals | Numerous scattered, small, raised crystals and an unevenly coated surface pattern |

Stabilizer* is TINUVIN ® 144 UV stabilizer.

TABLE 3

| Sample | Appearance of surface after removal of Imbibition Film of Concentration A sample | Appearance of surface after removal of Imbibition Film of Concentration B sample |
| --- | --- | --- |
| Example 1 and stabilizer* | No defects | Rare dimples No distortion of reflected light |
| Comparative Example 1 and stabilizer* | Scattered dimples, Some distortion of reflected light around dimples | Orange peel Severe distortion of reflected light |
| Comparative Example 2 and stabilizer* | Few dimples present Slight distortion around dimples | Fine orange peel Severe distortion of reflected light |

Stabilizer* is TINUVIN ® 144 UV stabilizer.

The results of Table 2 show the improved compatibility, i.e., solubility, of the Example 1 compound in the imbibition resin film as compared to the compounds of Comparative Examples 1 and 2. The imbibition resin film containing the compound of Example 1 demonstrates no observable defects when used at 2.4 weight percent and a few observable defects when used at 4.7 weight percent of the imbibition composition. The imbibition resin films containing Comparative Examples 1 and 2 demonstrate numerous defects at the lower concentration and additionally had unevenly coated surface patterns at the higher concentration.

The results of Table 3 show the effects of the imbibition compositions containing photochromic compounds of Example 1 and Comparative Examples 1 and 2 on the surface of the polymeric host. The lens imbibed with the composition containing Example 1 at 2.4 weight percent demonstrate no defects and only rare defects are observed with the composition containing 4.7 weight percent. The lenses imbibed with Comparative Examples 1 and 2 show dimple defects and some distortion of reflected light at the lower concentration and orange peel and severe distortion of reflected light at the higher concentrations.

The present invention has been described with reference to specific details of particular embodiments thereof. It is not intended that such details be regarded as limitations upon the scope of the invention except insofar as to the extent that they are included in the accompanying claims.

I claim:

1. A naphthopyran compound of 2H-naphtho[1,2-b]pyran structure, characterized by having in the 5 position, a group, $C(O)OR_1$, wherein $R_1$ is $(C_3-C_{12})$ cycloalkyl, mono$(C_1-C_6)$ alkyl substituted $C_3-C_{12}$ cycloalkyl, mono$(C_1-C_6)$alkoxy substituted $C_3-C_{12}$ cycloalkyl, halo$(C_3-C_{12})$cycloalkyl, $C_4-C_{12}$ bicyloalkyl or $C_7-C_{12}$ tricycloalkyl, said halo being bromo, chloro, fluoro or iodo.

2. The naphthopyran compound of claim 1 wherein said naphthopyran is represented by the following graphic formula:

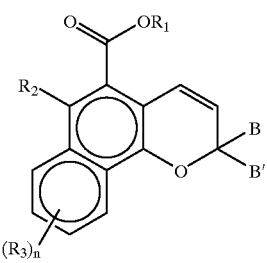

wherein, (a) $R_1$ is $C_3-C_{12}$ cycloalkyl, mono$(C_1-C_6)$alkyl substituted $C_3-C_{12}$ cycloalkyl, mono$(C_1-C_6)$alkoxy substituted $C_3-C_{12}$ cycloalkyl, halo$(C_3-C_{12})$cycloalkyl, $C_4-C_{12}$ bicycloalkyl or $C_7-C_{12}$ tricycloalkyl;

(b) $R_2$ is hydrogen, $C_1-C_6$ alkyl, $C_3-C_7$ cycloalkyl, phenyl, mono-, di-, or tri-substituted phenyl, the group —$OR_4$, wherein $R_4$ is hydrogen, $C_1-C_6$ alkyl, phenyl $(C_1-C_3)$alkyl, mono$(C_1-C_6)$alkyl substituted phenyl $(C_1-C_3)$alkyl, mono$(C_1-C_6)$alkoxy substituted phenyl $(C_1-C_3)$alkyl, $(C_1-C_6)$alkoxy$(C_2-C_4)$alkyl, $C_3-C_7$ cycloalkyl, mono$(C_1-C_4)$alkyl substituted $C_3-C_7$ cycloalkyl, $C_1-C_6$ haloalkyl, allyl, the group, —CH$(R_5)$X, wherein X is CN, $CF_3$, halogen or —C(O)W wherein W is —$OR_9$ or —N$(R_{10})R_{11}$, $R_5$ is hydrogen or $C_1-C_6$ alkyl, $R_9$ is hydrogen, allyl, $C_1-C_6$ alkyl, phenyl, mono$(C_1-C_6)$alkyl substituted phenyl, mono $(C_1-C_6)$alkoxy substituted phenyl, phenyl$(C_1-C_3)$ alkyl, mono$(C_1-C_6)$alkyl substituted phenyl$(C_1-C_3)$ alkyl, mono$(C_1-C_6)$alkoxy substituted phenyl$(C_1-C_3)$ alkyl, $C_1$–$C_6$ alkoxy($C_2$–$C_4$)alkyl, $C_1$–$C_6$ haloaklkyl or $R_1$, and $R_{10}$ and $R_{11}$ are each selected from the group consisting of hydrogen, $C_1$–$C_6$ alkyl, $C_3$–$C_7$ cycloalkyl, phenyl, mono-substituted phenyl and di-substituted phenyl, or $R_4$ is the group, —C(O)Y, wherein Y is hydrogen, $C_1$–$C_6$ alkyl, $C_1$–$C_6$ alkoxy, mono- or di-substituted or unsubstituted aryl groups phenyl or naphthyl, phenoxy, $C_1$–$C_6$ mono- or di-alkyl substituted phenoxy, $C_1$–$C_6$ mono- or di-alkoxy substituted phenoxy, $C_1$–$C_6$ alkylamino, phenylamino, $C_1$–$C_6$ mono- or di-alkyl substituted phenylamino, or $C_1$–$C_6$ mono- or di-alkoxy substituted phenylamino, said aryl substituents being selected from $C_1$–$C_6$ alkyl or $C_1$–$C_6$ alkoxy, said halogen or halo substituents being bromo, chloro, fluoro or iodo;

(c) each $R_3$ is $R_2$ and n is an integer selected from 0, 1, 2 or 3; and (d) B and B' are each selected from the group consisting of:
  (i) the unsubstituted, mono-, di- and tri-substituted aryl groups, phenyl and naphthyl;
  (ii) 9-julolidinyl and the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (d)(i) and (ii) being selected from the group consisting of hydroxy, aryl, mono($C_1$–$C_6$)alkoxyaryl, di($C_1$–$C_6$) alkoxyaryl, mono($C_1$–$C_6$)alkylaryl, di($C_1$–$C_6$) alkylaryl, haloaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy ($C_1$–$C_6$)alkoxy, aryl($C_1$–$C_6$)alkyl, aryl($C_1$–$C_6$) alkoxy, aryloxy, aryloxy($C_1$–$C_6$)alkyl, aryloxy ($C_1$–$C_6$)alkoxy, mono- and di-($C_1$–$C_6$)alkylaryl ($C_1$–$C_6$)alkyl, mono- and di-($C_1$–$C_6$)alkoxyaryl ($C_1$–$C_6$)alkyl, mono- and di-($C_1$–$C_6$)alkylaryl ($C_1$–$C_6$)alkoxy, mono- and di-($C_1$–$C_6$)alkoxyaryl ($C_1$–$C_6$)alkoxy, amino, mono($C_1$–$C_6$)alkylamino, di($C_1$–$C_6$)alkylamino, diarylamino, N-($C_1$–$C_6$) alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ haloalkyl, $C_1$–$C_6$ alkoxy, mono($C_1$–$C_6$)alkoxy ($C_1$–$C_4$)alkyl, acryloxy, methacryloxy and halogen, said aryl being phenyl or naphthyl and said halo and halogen being bromo, chloro, fluoro or iodo;
  (iii) the unsubstituted or mono-substituted groups, pyrazolyl, imidazolyl, pyridyl, pyrazolinyl, imidazolinyl, pyrrolinyl, phenothiazinyl, phenoxazinyl, phenazinyl or acridinyl, each of said substituents being selected from the group consisting of $C_1$–$C_6$ alkyl, $C_1$–$C_4$ alkoxy, phenyl, and halogen;
  (iv) monosubstituted phenyl, having a substituent at the para position that is a linking group, —($CH_2$)$_t$— or —O—($CH_2$)$_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran;
  (v) the group represented by the following graphic formula:

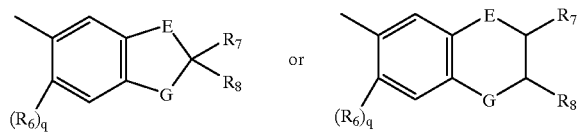

wherein E is methylene or oxygen and G is oxygen or substituted nitrogen, provided that when G is substituted nitrogen, E is methylene, said nitrogen substituents being selected from the group consisting of hydrogen, $C_1$–$C_6$ alkyl and $C_2$–$C_6$ acyl; each $R_6$ is $C_1$–$C_6$ alkyl, $C_1$–$C_6$ alkoxy, hydroxy, or halogen; $R_7$ and $R_8$ are each hydrogen or $C_1$–$C_6$ alkyl; and q is the integer 0, 1 or 2;

(vi) $C_1$–$C_6$ alkyl, $C_1$–$C_6$ haloalkyl, $C_1$–$C_6$ alkoxy ($C_1$–$C_4$)alkyl, $C_3$–$C_{12}$ cycloalkyl, mono($C_1$–$C_6$) alkoxy($C_3$–$C_{12}$)cycloalkyl, mono($C_1$–$C_6$)alkyl ($C_3$–$C_{12}$)-cycloalkyl, halo($C_3$–$C_{12}$)cycloalkyl and $C_4$–$C_{12}$ bicycloalkyl; and
  (vii) the group represented by the following graphic formula:

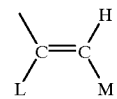

wherein L is hydrogen or $C_1$–$C_4$ alkyl and M is selected from the unsubstituted, mono-, and di-substituted members of the group consisting of naphthyl, phenyl, furanyl and thienyl, each of said group substituents being $C_1$–$C_4$ alkyl, $C_1$–$C_4$ alkoxy or halogen; or (e) B and B' taken together form fluoren-9-ylidene, mono-, or di-substituted fluoren-9-ylidene or a member selected from the group consisting of saturated $C_3$–$C_{12}$ spiro-monocyclic hydrocarbon rings, saturated $C_4$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy and halogen.

3. The naphthopyran of claim 2 wherein:
(a) $R_1$ is $C_3$–$C_{10}$ cycloalkyl, mono($C_1$–$C_3$)alkyl substituted $C_3$–$C_{10}$ cycloalkyl, mono ($C_1$–$C_3$)alkoxy substituted $C_3$–$C_{10}$ cycloalkyl, chloro($C_3$–$C_{10}$)fluoro($C_1$–$C_3$) cycloalkyl, $C_4$–$C_{10}$ bicycloalkyl or $C_7$–$C_{10}$ tricycloalkyl;
(b) $R_2$ is hydrogen, $C_1$–$C_3$ alkyl, $C_3$–$C_5$ cycloalkyl, phenyl, mono- or di-substituted phenyl or —$OR_4$, wherein $R_4$ is hydrogen, $C_1$–$C_3$ alkyl, or the group, —CH($R_5$)X, wherein X is CN or —C(O)W wherein W is —$OR_9$ or —N($R_{10}$)$R_{11}$, $R_5$ is hydrogen or methyl, $R_9$ is hydrogen, $C_1$–$C_4$ alkyl, phenyl, mono($C_1$–$C_4$)alkyl substituted phenyl, mono($C_1$–$C_4$)alkoxy substituted phenyl, phenyl($C_1$–$C_2$)alkyl, mono($C_1$–$C_4$)alkyl substituted phenyl($C_1$–$C_2$)alkyl, mono($C_1$–$C_4$)alkoxy ($C_2$–$C_3$)alkyl, $C_1$–$C_4$ haloalkyl or $R_1$, and $R_{10}$ and $R_{11}$ are each selected from the group consisting of hydrogen, $C_1$–$C_4$ alkyl, $C_5$–$C_7$ cycloalkyl, phenyl, mono-substituted phenyl and di-substituted phenyl; or $R_4$ is the group —C(O)Y wherein Y is $C_1$–$C_3$ alkyl or $C_1$–$C_3$ alkoxy, said phenyl substituents being $C_1$–$C_3$ alkyl or $C_1$–$C_3$ alkoxy and said halo being chloro or fluoro;
(c) each $R_3$ is hydrogen, $C_1$–$C_4$ alkyl, $C_3$–$C_{10}$ cycloalkyl, phenyl, mono- or di-substituted phenyl, said phenyl substituents being $C_1$–$C_3$ alkyl or $C_1$–$C_3$ alkoxy, and n is the integer 0, 1 or 2;

(d) B and B' are each selected from the group consisting of:
  (i) phenyl, mono-substituted and di-substituted phenyl;
  (ii) the unsubstituted, mono- and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in (d)(i) and (ii) being selected from the group consisting of hydroxy, aryl, aryloxy, aryl($C_1$–$C_3$)alkyl, amino, mono($C_1$–$C_3$)alkylamino, di($C_1$–$C_3$)alkylamino, N—($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy ($C_1$–$C_3$)alkyl, chloro and fluoro;
  (iii) the group represented by the following graphic formula:

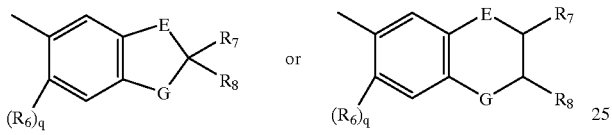

wherein E is methylene and G is oxygen, $R_6$ is $C_1$–$C_3$ alkyl or $C_1$–$C_3$ alkoxy; $R_7$ and $R_8$ are each hydrogen or $C_1$–$C_4$ alkyl; and q is 0 or 1;
  (iv) $C_1$–$C_4$ alkyl; and
  (v) the group represented by the following graphic formula:

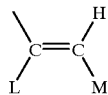

wherein L is hydrogen or methyl, M is phenyl or mono-substituted phenyl, said phenyl substituent being $C_1$–$C_3$ alkyl, $C_1$–$C_3$ alkoxy or fluoro; or (e) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

4. The naphthopyran of claim 3 wherein:
(a) $R_1$ is $C_3$–$C_7$ cycloalkyl;
(b) $R_2$ is hydrogen or $C_1$–$C_3$ alkyl
(c) $R_3$ is hydrogen or $C_1$–$C_3$ alkyl, and n is the integer 0 or 1;
(d) B and B' are each selected from the group consisting of:
  (i) phenyl, mono- and di-substituted phenyl;
  (ii) the unsubstituted, mono- and di-substituted heteroaromatic groups furanyl, benzofuran-2-yl, thienyl and benzothien-2-yl, each of said phenyl and heteroaromatic substituents in (d)(i) and (ii) being selected from the group consisting of hydroxy, $C_1$–$C_3$ alkyl, $C_1$–$C_3$ alkoxy, phenyl, indolino, fluoro and chloro;
  (iii) the group represented by the following graphic formula:

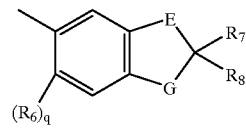

wherein E is methylene and G is oxygen, $R_6$ is $C_1$–$C_3$ alkyl or $C_1$–$C_3$ alkoxy; $R_7$ and $R_8$ are each hydrogen or $C_1$–$C_3$ alkyl; and q is 0 or 1; or (e) B and B' taken together form fluoren-9-ylidene, adamantylidene, bornylidene, norbornylidene, or bicyclo[3.3.1]nonan-9-ylidene.

5. A naphthopyran compound selected from the group consisting of:
(a) 2,2-Diphenyl-5-cyclohexyloxycarbonyl-8-methyl-[2H]-naphtho[1,2-b]pyran;
(b) 2,2-Bis(4-methoxyphenyl)-5-cyclopropyloxycarbonyl-6-methoxy-[2H]-naphtho[1,2-b]pyran;
(c) 2,2-Bis(4-methoxyphenyl)-5-cyclooctyloxycarbonyl-6-(ethoxycarbonyl)methoxy-[2H]-naphtho[1,2-b]pyran;
(d) 2,2-Bis(4-methylphenyl)-5-cyclohexyloxycarbonyl-6-(methoxycarbonyloxy)-[2H]-naphtho[1,2-b]pyran;
(e) 2,2-Diphenyl-5-cyclopropyloxycarbonyl-6-acetoxy-[2H]-naphtho[1,2-b]pyran;
(f) 2,2-Bis(4-methoxyphenyl)-5-cyclooctyloxycarbonyl-6-methyl-[2H]-naphtho[1,2-b]pyran;
(g) 2,2-Bis(4-methoxyphenyl)-5-cycloheptyloxycarbonyl-6-methyl-9-methoxy-[2H]-naphtho[1,2-b]pyran;
(h) 2-(4-Methoxyphenyl)-2-(2-methyl,2,3-dihydrobenzofuran-5-yl)-5-cyclobutyloxycarbonyl-6-(ethoxycarbonyl)methoxy-[2H]-naphtho[1,2-b]pyran;
(i) 2-phenyl-2-(2-dibenzofuryl)-5-cyclohexyloxycarbonyl-8-methyl-[2H]-naphtho[1,2-b]pyran;
(j) 2,2-diphenyl-5-cyclohexyloxycarbonyl-8-methoxy-[2H]-naphtho[1,2-b]pyran;
(k) 2-phenyl-2-(4-methoxyphenyl)-5-cyclohexyloxycarbonyl-8-methoxy-[2H]-naphtho[1,2-b]pyran; and
(1) 2-phenyl-2-(4-methylphenyl)-5-cyclohexyloxycarbonyl-8-methoxy-[2H]-naphtho[1,2-b]pyran.

6. A photochromic article comprising in combination, a polymeric organic host material and a photochromic amount of the naphthopyran compound of claim 1.

7. The photochromic article of claim 6 wherein the polymeric organic host material is selected from the group consisting of polyacrylates, polymethacrylates, poly ($C_1$–$C_{12}$) alkyl methacrylates, polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

8. The photochromic article of claim 6 wherein the naphthopyran compound is present in an amount of from 0.05 to 2.0 milligram per square centimeter of polymeric organic host material surface to which the photochromic substance(s) is incorporated or applied.

9. The photochromic article of claim 6 wherein said polymeric organic host material is an optical element.

10. The photochromic article of claim 9 wherein said optical element is a lens.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 2.

12. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 4.

13. A photochromic article comprising, in combination, a solid substrate and a photochromic amount of each of (a) at least one naphthopyran compound of claim 1, and (b) at least one other organic photochromic compound having at least one activated absorption maxima within the range of between 400 and 700 nanometers.

14. A photochromic article comprising a polymerizate of an optical organic resin monomer and a photochromic amount of the naphthopyran compound of claim 1.

15. The photochromic article of claim 14 wherein the refractive index of the polymerizate is from about 1.48 to about 1.75.

16. The photochromic article of claim 14 wherein the polymerizate is an optical element.

17. The photochromic article of claim 16 wherein said optical element is a lens.

18. A photochromic article comprising, in combination, a solid substrate and on at least one surface thereof a cured coating of a coating composition having a photochromic amount of the naphthopyran compound of claim 1.

19. The photochromic article of claim 18 wherein said coating composition is selected from the group consisting of a polymeric coating composition, paint and ink.

20. The photochromic article of claim 18 wherein the substrate is selected from the group consisting of glass, masonry, textiles, ceramics, metals, wood, paper and polymeric organic materials.

21. A photochromic article comprising, in combination, a solid substrate and on at least one surface thereof a cured coating of a coating composition having a photochromic amount of the naphthopyran compound of claim 2.

22. A photochromic article comprising, in combination, a solid substrate and on at least one surface thereof a cured coating of a coating composition having a photochromic amount of the naphthopyran compound of claim 4.

* * * * *

UNITED STATES PATENT AND TRADEMARK OFFICE
CERTIFICATE OF CORRECTION

PATENT NO.   : 6,340,766 B1
DATED        : January 22, 2002
INVENTOR(S)  : Jibin Lin It is certified that error appears in the above-identified patent and that said Letters Patent is hereby corrected as shown below:

Column 24,
Line 20, delete "C4-$C_{12}$" and insert -- $C_4$-$C_{12}$ --.
Line 46, delete "chloro($C_3$-$C_{10}$)fluoro($C_1$-$C_3$)cycloalkyl" and insert -- chloro($C_3$-$C_{10}$)cycloalkyl, fluoro($C_1$-$C_3$)cycloalkyl, --.

Signed and Sealed this

Twenty-second Day of November, 2005

JON W. DUDAS
*Director of the United States Patent and Trademark Office*